United States Patent
Yan

(10) Patent No.: US 10,006,758 B2
(45) Date of Patent: Jun. 26, 2018

(54) LOCATING THE BODY SURFACE POSITION OF A CT SCANNED SUBJECT

(71) Applicant: Shenyang Neusoft Medical Systems Co., Ltd., Shenyang (CN)

(72) Inventor: Gang Yan, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 353 days.

(21) Appl. No.: 14/923,448

(22) Filed: Oct. 27, 2015

(65) Prior Publication Data

US 2016/0117826 A1 Apr. 28, 2016

(30) Foreign Application Priority Data

Oct. 27, 2014 (CN) .......................... 2014 1 0582659
Sep. 10, 2015 (CN) .......................... 2015 1 0573819

(51) Int. Cl.
 *A61B 6/03* (2006.01)
 *A61B 6/00* (2006.01)
 (Continued)

(52) U.S. Cl.
 CPC .......... *G01B 11/0608* (2013.01); *A61B 6/032* (2013.01); *A61B 6/488* (2013.01);
 (Continued)

(58) Field of Classification Search
 CPC ... G01B 11/0608; G01B 11/26; G01B 11/022; A61B 6/5211; A61B 6/544; A61B 6/545; A61B 5/0033; A61B 5/055; A61B 5/0555; A61B 6/02; A61B 6/025; A61B 6/027; A61B 6/03; A61B 6/032; A61B 6/035; A61B 6/037; A61B 6/52; A61B 6/5205;
 (Continued)

(56) References Cited

U.S. PATENT DOCUMENTS

2002/0118280 A1 8/2002 Medlar et al.
2004/0081341 A1 4/2004 Cherek et al.
(Continued)

FOREIGN PATENT DOCUMENTS

CN 102805636 A * 12/2012
CN 103181775 A 7/2013
(Continued)

*Primary Examiner* — Behrooz Senfi
*Assistant Examiner* — Kathleen Walsh
(74) *Attorney, Agent, or Firm* — Kilpatrick Townsend & Stockton LLP

(57) ABSTRACT

CT scanning techniques and systems thereof are disclosed. In various embodiments, a body surface measuring point of a subject on a scanning bed can be identified according to a frontal image captured by a first image capturing device. A measuring projection angle can be acquired using the body surface measuring point. A lateral image of the subject can be captured using a second image capturing device. Based on the lateral image, a vertical distance between the body surface measuring point and the scanning bed, a current height and the initial height of the scanning bed, a horizontal position of the body surface measuring point under the initial height can be acquired. A horizontal position of the body surface measuring point under the current height can be determined based on above acquired parameters.

13 Claims, 2 Drawing Sheets

(51) Int. Cl.
*G01B 11/06* (2006.01)
*G01B 11/26* (2006.01)
*A61B 6/04* (2006.01)

(52) U.S. Cl.
CPC ............ *A61B 6/5211* (2013.01); *A61B 6/544* (2013.01); *A61B 6/545* (2013.01); *G01B 11/26* (2013.01)

(58) Field of Classification Search
CPC ... A61B 6/5217; A61B 6/5233; A61B 6/5229; A61B 6/5235; A61B 6/5241; A61B 6/5247; A61B 6/5264; A61B 6/527; A61B 6/5276; A61B 6/5285; A61B 6/5288; A61B 6/5294; A61B 8/13; A61B 8/14; A61B 8/145; A61B 8/15; A61B 8/46; A61B 8/52; A61B 8/5207; A61B 8/5215; A61B 8/5223; A61B 8/523; A61B 8/5238; A61B 8/5246; A61B 8/5253; A61B 8/5276; A61B 8/5284; A61B 8/5292; A61B 6/04; A61B 6/488; A61B 6/5282; G01N 2223/506; G01N 23/046; G06T 2207/10081; G06T 2207/30196; G06T 7/0042; G06T 7/70; G06T 7/73; G06T 7/74; G06T 7/75; G06T 7/77; G06T 2207/10072; G06T 2207/10076; G06T 2207/10084; G06T 2207/10088; G06T 2207/10092; G06T 2207/10096; G06T 2207/10101; G06T 2207/10104; G06T 2207/10108; G06T 2207/10112; G06T 2211/40; G06T 2211/404; G06T 2211/408; G06T 2211/412; G06T 2211/416; G06T 2211/421; G06T 2211/424; G06T 2211/428; G06T 2211/432; G06T 2211/436; H04N 5/247; G01C 11/00; G01R 33/20; G01R 33/5608
USPC ................... 348/61, 135; 382/131
See application file for complete search history.

(56) References Cited

U.S. PATENT DOCUMENTS

| | | | |
|---|---|---|---|
| 2004/0082852 A1 | 4/2004 | Cherek et al. | |
| 2007/0003020 A1* | 1/2007 | Hsieh | A61B 6/032 378/207 |
| 2009/0088621 A1* | 4/2009 | Xu | A61B 6/032 600/407 |
| 2009/0147909 A1* | 6/2009 | Yoda | A61B 6/032 378/4 |
| 2010/0074404 A1* | 3/2010 | Ito | G01N 23/223 378/42 |
| 2010/0198112 A1 | 8/2010 | Maad | |
| 2011/0135190 A1 | 6/2011 | Maad | |
| 2011/0274240 A1* | 11/2011 | Sugaya | A61B 6/032 378/16 |
| 2015/0313569 A1* | 11/2015 | Stevens | A61B 6/032 378/8 |

FOREIGN PATENT DOCUMENTS

| | | | |
|---|---|---|---|
| CN | 103767722 A | * | 5/2014 |
| CN | 203736217 U | | 7/2014 |

* cited by examiner

LOCATING THE BODY SURFACE POSITION OF A CT SCANNED SUBJECT

The present application claims the priority to Chinese Patent Applications No. 201410582659.2, filed with the Chinese State Intellectual Property Office on Oct. 27, 2014, and Chinese Patent Applications No. 201510573819.1, filed with the Chinese State Intellectual Property Office on Sep. 10, 2015, both of which are incorporated herein by reference in their entireties.

BACKGROUND

In a clinical computed tomography (CT) scanning for a subject, an X-ray pilot scanning is usually performed for locating the region of interesting (ROI) of the subject. However, when an X-ray beam is irradiated onto the subject, cells of the subject may be degraded, damaged or even die, and an injury such as alopecia, skin burn, vision disorder, or even blood cancer may be caused to the subject. Thus, how to reduce the damage caused by an X-ray irradiation to the subject during a CT scanning is an increasing concerned issue to be further researched and addressed.

The present disclosure provides a method and system for locating the body surface position of a CT scanned subject, which may reduce the damage caused by an X-ray irradiation to the subject for obtaining exact position information of the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

The present invention is directed to CT techniques.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

For reducing one or more damages caused by an X-ray irradiation to a CT scanned subject during a CT scanning, embodiments provide a technique for capturing an image of a body surface position of the CT scanned subject using an image capturing device (such as a video camera), and calculating positions of a measuring point based on the captured image to obtain a start scanning point of the ROI of the subject, rather than performing a conventional CT pilot scanning.

Figure 1:
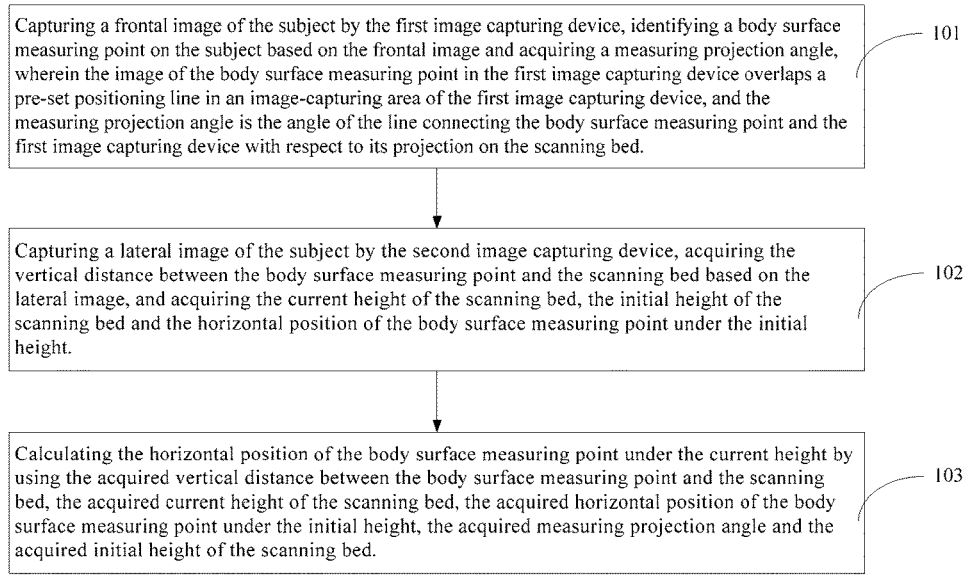
FIG. 1 is a schematic flowchart illustrating a method for locating the body surface position of a CT scanned subject according to an example of the present disclosure.
Figures 2A, 2B:
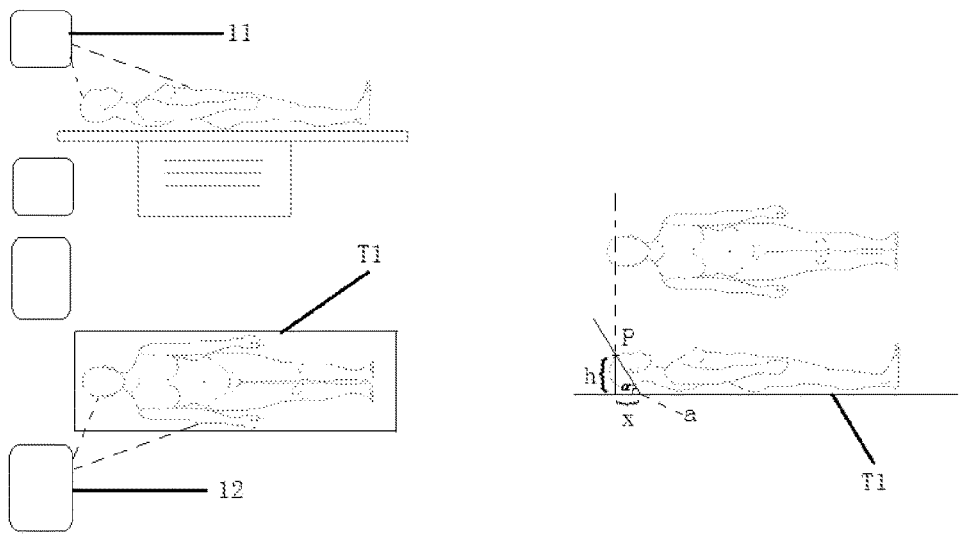
FIG. 2A and FIG. 2B are schematic diagrams illustrating locating the body surface position of a CT scanned subject by a first image capturing device and a second image capturing device according to an example of the present disclosure.

FIG. 1 illustrates a method for locating the body surface position of a CT scanned subject according to an example of the present disclosure. The method illustrated in FIG. 1 may be employed in a CT scanning system shown in FIG. 2A including a first image capturing device 11, a second image capturing device 12, and a CT scanner and a scanning bed T1. Referring to FIG. 2, the first image capturing device 11 is located right above the scanning bed T1 for capturing a frontal image of the subject on the scanning bed, and the second image capturing device 12 is located at a lateral side of the scanning bed T1 for capturing a lateral image of the subject on the scanning bed T1. The scanning bed is provided with a baseline (not shown), and the image of the baseline in the first image capturing device 11 shall match a pre-set positioning line in an image-capturing area of the first image capturing device 11. The method illustrated in FIG. 1 will be described with reference to FIG. 2 and may be applied before a diagnostic CT scanning. As shown, the method can comprise:

Block 101: wherein, a frontal image of the subject by the first image capturing device may be captured; a body surface measuring point on the subject can be identified based on the frontal image; and a measuring projection angle can be acquired, wherein the image of the body surface measuring point in the first image capturing device overlaps a pre-set positioning line in an image-capturing area of the first image capturing device, and the measuring projection angle is the angle of the line connecting the body surface measuring point and the first image capturing device with respect to its projection on the scanning bed.

The scanning bed that can be used the method, such as T1 shown in FIG. 2, may be a carbon-lead bed of high strength for loading a subject into/out of the CT scanning aperture in a CT scanning system or a PET-CT scanning system. During a diagnostic CT scanning, the subject is usually on the scanning bed that can be moved through a scanning aperture with a rack, and an X-ray beam irradiated from the irradiation source of the CT scanner may penetrate through the body of the subject to acquire a diagnostic image.

According to the present disclosure, parameters for locating a body surface position of a subject (hereinafter "body surface locating parameters") of a CT scanning system can be corrected before the CT scanning system is shipped, so as to make it is possible to locate the subject by capturing images for the body surface. In an example, firstly, a baseline is provided on the scanning bed. The baseline is usually parallel with the short sides of the scanning bed and is vertical to the direction of loading the subject into the scanning aperture (hereinafter "Z axial direction"). The baseline may be a slim metal wire parallel with the short sides of the scanning bed, such as an iron wire having a diameter of about 1 mm. Of course, the baseline in accordance with the present disclosure is not limited to this. When the baseline is already set, the horizontal position of the scanning bed may be further calibrated in such a way that the baseline captured by the first image capturing device, such as the first image capturing device 11 shown in FIG. 2, can match a pre-set positioning line in the first image capturing device.

It should be understood that in the present disclosure, the position of the positioning line in the first image capturing device can vary as long as the positioning line is vertical to the Z-axial direction. For example, in practical application scenarios, the positioning line may be an edge line of the image-capturing area of the first image capturing device, which is vertical to the Z-axial direction. When the image of the baseline in the first image-capturing device matches the pre-set positioning line in the first image capturing device, the angle of the line connecting the baseline and the first image capturing device with respect to its projection on the scanning bed (hereinafter "positioning projection angle") and the initial height of the scanning bed may be calculated according to a pre-determined algorithm.

Further, in the present disclosure, the first image capturing device may capture a frontal image of the subject to identify a body surface measuring point for the subject, wherein the image of the body surface measuring point for the subject in the first image capturing device overlaps the pre-set positioning line in the image-capturing area of the first image capturing device. Since related parameters of the CT scanning system has been corrected before the CT scanning system is shipped, if the image of the body surface measuring point overlaps the positioning line of the first image capturing device, the measuring projection angle is the same as the positioning projection angle. Since the positioning projection angle is known before the CT scanning system is delivered, the measuring projection angle can be acquired. FIG. 2A illustrates a frontal image schematic of the subject captured by the first image capturing device 11 in which two dashed lines represent the image-capturing area of the first image capturing device. In FIG. 2B, point P represents the body surface measuring point of the subject, and when the image of the point P in the first image capturing device overlaps the positioning line, the measuring projection angle may be the same as the positioning projection angle, that is, the angle of α.

Block 102: wherein, a lateral image of the subject may be captured by the second image capturing device; the vertical distance between the body surface measuring point and the scanning bed may be acquired by using a lateral image of the subject captured by a second image capturing device; and the current height of the scanning bed, the initial height of the scanning bed and the horizontal position of the body surface measuring point under the initial height may be acquired.

In the above example, a lateral image of the subject is captured by the second image capturing device such as T2 shown in FIG. 2A, so as to acquire the vertical distance between the body surface measuring point and the scanning bed such as the vertical distance h illustrated in FIG. 2B according to an algorithm which is pre-set before the CT scanning system delivered.

Figure 3:
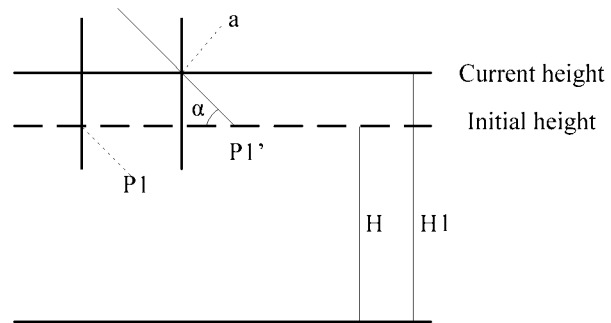
FIG. 3 is a schematic diagram illustrating parameters for locating the body surface position of a CT scanned subject by the first image capturing device and the second image capturing device.

Further, the current height of the scanning bed and the horizontal position of the body surface measuring point under the initial height also can be acquired according to the algorithm which is pre-set before the CT scanning system is delivered. In an example, the current height, showed as H1 in FIG. 3, can be calculated with the initial height and the vertical relative displacement of the scanning bed from the initial position to the current position. And the horizontal position of the body surface measuring point under the initial height, which is showed as P1' in FIG. 3, can be calculated with the horizontal position of the baseline and the horizontal relative displacement of the scanning bed from the initial position to the current position.

Block 103: wherein, the horizontal position of the body surface measuring point under the current height is calculated by using the acquired vertical distance between the body surface measuring point and the scanning bed, the acquired current height of the scanning bed, the acquired horizontal position of the body surface measuring point under the initial height, the acquired measuring projection angle, and the acquired initial height of the scanning bed, so as to locate the body surface measuring point.

Referring to FIG. 1, the vertical distance h between the body surface measuring point and the scanning bed, the current height H1 of the scanning bed, the horizontal position P1' of the body surface measuring point under the initial height, the measuring projection angle α and the initial height H of the scanning bed may be acquired through Block 101 and Block 102. Thus, assuming that the extension line of the line connecting the body surface measuring point and the first image capturing device crosses with the scanning bed at a crossing point a, the horizontal position $w_a$ of the crossing point a under the initial height can be calculate through the following equation (1):

$$w_a = P1' - (H1 - H) * \arctan \alpha \quad (1)$$

When the $w_a$ is acquired through the above equation (1), the horizontal position of the body surface measuring point P under the current height can be calculated through the following equation (2):

$$P = w_a - x \quad (2)$$

In which, the x is the distance between the horizontal position of the body surface measuring point and the horizontal position $w_a$ of the crossing point a under the initial height. The x in the equation (2) can be acquired through the following equation (3):

$$x = h * \arctan \alpha \quad (3)$$

In the equation (3), the vertical distance h between the body surface measuring point and the scanning bed, and the measuring projection angle α both are already known, and thus the value of x can be calculated through the equation (3). In the equation (2), the values of $w_a$ and x can be calculated through the equations (1) and (3) respectively, and thus the horizontal position of the body surface measuring point under the current height can be acquired so as to locate the body surface measuring point, i.e., get the exact position information of the body surface measuring point.

In the present disclosure, the horizontal position of the body surface measuring point is acquired by using the first image capturing device and the second image capturing device, which can prevent the damage caused by the X-ray irradiation to the subject in a conventional pilot scanning and improve the health condition of the patient.

Figure 4:
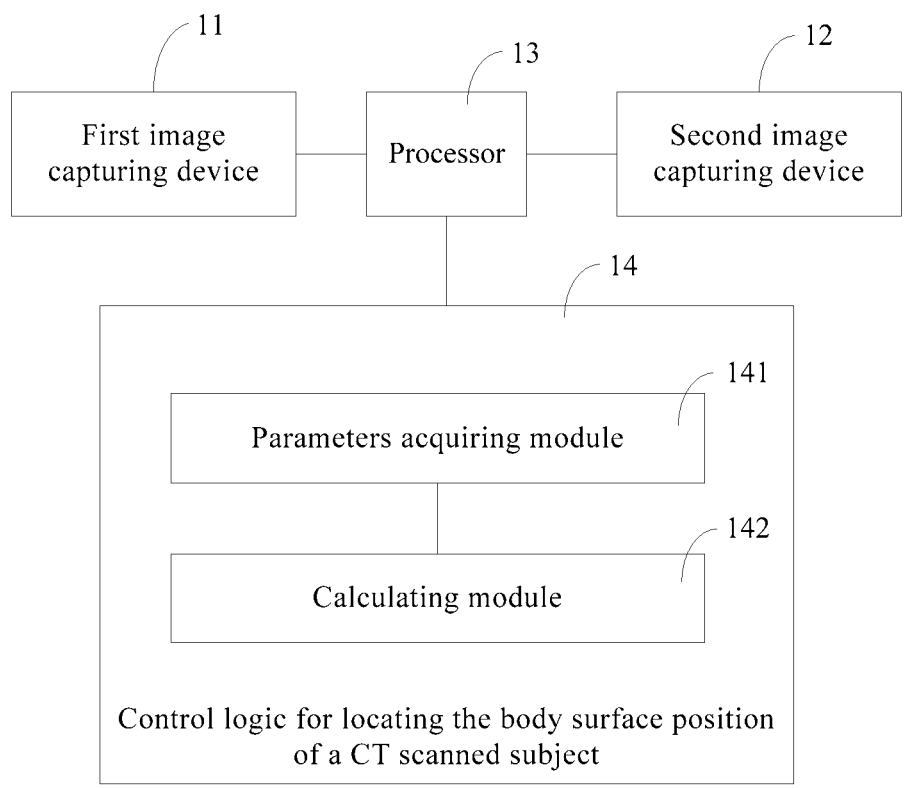
FIG. 4 is a schematic block diagram illustrating the structure of a system for locating the body surface position of a CT scanned subject according to an example of the present disclosure.

In another example, the present disclosure provides a control logic for locating the body surface position of a CT scanned subject. FIG. 4 illustrates a control logic 14 for locating the body surface position of a CT scanned subject. The control logic provided in FIG. 4 may be applied in a CT scanning system as shown in FIG. 2. As shown in FIG. 4, a first image capturing device 11 and a second image capturing device 12 are respectively connected to a processor 13 which may execute machine readable instructions corresponding to the control logic 14. The control logic 14 may include a parameter acquiring module 141 and a calculating module 142. The parameter acquiring module 141 is further connected with the calculating module 142.

The parameter acquiring module 141 is configured to acquire a measuring projection angle according to a frontal image captured by the first image capturing device 11, acquire the vertical distance between a body surface measuring point and the scanning bed according to the lateral image captured by the second image capturing device 12, and acquire the initial height and the current height of the scanning bed and the horizontal position of the body surface measuring point under the initial height. Wherein, the measuring projection angle is the angle of the line connecting the body surface measuring point and the first image capturing device with respect to its projection on the scanning bed.

The calculating module 142 is configured to calculate the horizontal position of the body surface measuring point under the current height according to the acquired vertical distance between the body surface measuring point and the scanning bed, the acquired current height of the scanning bed, the horizontal position of the body surface measuring point under the initial height, the acquired measuring projection angle and the initial height of the scanning bed, so as to locate the body surface measuring point, i.e., get the exact position information of the body surface measuring point.

Particularly, the calculating module 142 may acquire the horizontal position of the body surface measuring point under the current height through the following equation:

$$P = P1' - (H1 - H + h) * \arctan \alpha$$

Wherein, the P is the horizontal position of the body surface measuring point under the current height, the P1' is the horizontal position of the body surface measuring point under the initial height, the H1 is the current height of the scanning bed, the H is the initial height of the scanning bed, the h is the vertical distance between the body surface measuring point and the scanning bed, the α is the measuring projection angle.

The example below is implemented with software, which describes how the CT scanning system runs the control logic 14 for locating the body surface position of a CT scanned subject. In this example, the control logic 14 for locating the body surface position of a CT scanned subject should be understood as computer-readable instructions stored in a machine-readable storage medium. When the processor of the CT scanning system executes the control logic for locating the body surface position of a CT scanned subject, the processor invokes instructions of corresponding functional blocks of the control logic so as to:

acquire a measuring projection angle according to a frontal image captured by a first image capturing device, wherein the measuring projection angle is the angle of the line connecting a body surface measuring point and the first image capturing device with respect to its projection on the scanning bed;

acquire the vertical distance between the body surface measuring point and the scanning bed according to a lateral image captured by a second image capturing device, acquire the initial height of the scanning bed, the current height of the scanning bed and the horizontal position of the body surface measuring point under the initial height; and calculate the horizontal position of the body surface measuring point under the current height according to the acquired vertical distance between the body surface measuring point and the scanning bed, the acquired current height of the scanning bed, the horizontal position of the body surface measuring point under the initial height, the measuring projection angle and the initial height of the scanning bed, so as to locate the body surface measuring point, i.e., find the exact position information of the body surface measuring point.

Particularly, the horizontal position of the body surface measuring point under the current height may be calculated through the following equation:

$$P = P1' - (H1 - H + h) * \arctan \alpha$$

Wherein, the P is the horizontal position of the body surface measuring point under the current height, the P1' is the horizontal position of the body surface measuring point under the initial height, the H1 is the current height of the scanning bed, the H is the initial height of the scanning bed, the h is the vertical distance between the body surface measuring point and the scanning bed, and the α is the measuring projection angle.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for locating a body surface position of a CT scanned subject, the method being applied before a diagnostic CT scanning, the method comprising:
   capturing a frontal image of a subject on a scanning bed by a first image capturing device,
   identifying a body surface measuring point based on the frontal image such that an image of the body surface measuring point in the first image capturing device overlaps a predetermined positioning line in an image-capturing area of the first image capturing device,
   acquiring a measuring projection angle, wherein the measuring projection angle is the angle of the line connecting the body surface measuring point and the first image capturing device with respect to its projection on the scanning bed;
   capturing a lateral image of the subject by a second image capturing device;
   acquiring a vertical distance between the body surface measuring point and the scanning bed based on the lateral image,
   based on the lateral image of the subject, acquiring a current height of the scanning bed, an initial height of the scanning bed, and a horizontal position of the body surface measuring point under the initial height; and
   calculating a horizontal position of the body surface measuring point under the current height according to the vertical distance between the body surface measuring point and the scanning bed, the current height of the scanning bed, the horizontal position of the body surface measuring point under the initial height, the measuring projection angle and the initial height of the scanning bed.

2. The method of claim 1, wherein acquiring the measuring projection angle comprises:
   providing a baseline on the scanning bed, wherein the baseline is parallel with a short side of the scanning bed;
   acquiring a positioning projection angle when an image of the baseline in the first image capturing device matches the positioning line predetermined in the first image capturing device, wherein the positioning projection angle is the angle of the line connecting the baseline and the first image capturing device with respect to its projection on the scanning bed; and
   using the positioning projection angle as the measuring projection angle.

3. The method of claim 1, wherein the horizontal position of the body surface measuring point under the current height is calculated through the following equation:

$$P = P1' - (H1 - H + h) * \arctan \alpha$$

wherein, the P is the horizontal position of the body surface measuring point under the current height,
   the P1' is the horizontal position of the body surface measuring point under the initial height,
   the H1 is the current height of the scanning bed,
   the H is the initial height of the scanning bed,
   the h is the vertical distance between the body surface measuring point and the scanning bed, and
   the α is the measuring projection angle.

4. The method of claim 1, wherein the current height is calculated with the initial height of the scanning bed and a vertical relative displacement of the scanning bed from an initial position to a current position.

5. The method of claim 1, wherein the horizontal position of the body surface measuring point under the initial height is calculated with a horizontal position of a baseline provided on the scanning bed and a horizontal relative displacement of the scanning bed from an initial position to a current position.

6. A system for locating a body surface position of a CT scanned subject, the system comprising a first image capturing device, a second image capturing device and a processor, wherein the first image capturing device and the second image capturing device are connected to the processor respectively, and the processor is configured to execute machine readable instructions, the machine-readable including instructions corresponding to a control logic for locating the body surface position of a CT scanned subject stored and, when executed by the processor, causing the processor to:
   acquire a measuring projection angle according to a frontal image of a subject on a scanning bed captured by the first image capturing device, wherein the measuring projection angle is the angle of the line connecting a body surface measuring point and the first image capturing device with respect to its projection on the scanning bed, and wherein the measuring projection angle is acquired when the image of the body surface measuring point in the first image capturing device overlaps a pre-set positioning line in the image-capturing area of the first image capturing device;
   acquire a vertical distance between the body surface measuring point and the scanning bed according to a lateral image of the subject captured by the second image capturing device,
   acquire an initial height of the scanning bed, a current height of the scanning bed and a horizontal position of the body surface measuring point under the initial height; and
   calculate the horizontal position of the body surface measuring point under the current height according to the acquired vertical distance between the body surface measuring point and the scanning bed, the acquired current height of the scanning bed, the acquired horizontal position of the body surface measuring point under the initial height, the acquired measuring projection angle and the acquired initial height of the scanning bed.

7. The system of claim 6, wherein the horizontal position of the body surface measuring point under the current height is calculated through the following equation:

$$P = P1' - (H1 - H + h) * \arctan \alpha$$

wherein, the P is the horizontal position of the body surface measuring point under the current height,
the P1' is the horizontal position of the body surface measuring point under the initial height,
the H1 is the current height of the scanning bed,
the H is the initial height of the scanning bed,
the h is the vertical distance between the body surface measuring point and the scanning bed, and
the α is the measuring projection angle.

8. A computer-implemented method for locating a body surface position of on a subject under a computed tomography (CT) scanning system, the CT scanning system comprising a scanning bed, the method comprising:
capturing a frontal image of the subject using a first image capturing device that has an image-capturing area, wherein a predetermined positioning line is in the image capturing area;
identifying a body surface measuring point on the subject using the frontal image such that the body surface measuring point overlaps the predetermined positioning line as captured in the frontal image;
determining a measuring projection angle with respect to the scanning bed for the body surface measuring point;
capturing a lateral image of the subject using a second capturing device;
based on the lateral image of the subject, determining a vertical distance between the body surface measuring point and the scanning bed, a current height of the scanning bed, an initial height of the scanning bed, and a horizontal position of the body surface measuring point under the initial height; and
calculating a horizontal position of the body surface measuring point under the current height based on the vertical distance between the body surface measuring point and the scanning bed, the current height of the scanning bed, the horizontal position of the body surface measuring point under the initial height, the measuring projection angle and the initial height of the scanning bed.

9. The method of claim 8, wherein the measuring projection angle is determined by connecting a line between the body surface measuring point and the first image capturing device, and the measuring projection angle is an angle where the line intersects the scanning bed.

10. The method of claim 8, wherein the horizontal position of the body surface measuring point under the current height is calculated through the following equation:

$$P = P1' - (H1 - H + h) * \arctan \alpha$$

wherein, P is the horizontal position of the body surface measuring point under the current height,
P1' is the horizontal position of the body surface measuring point under the initial height,
H1 is the current height of the scanning bed,
H is the initial height of the scanning bed,
h is the vertical distance between the body surface measuring point and the scanning bed, and
α is the measuring projection angle.

11. The method of claim 8, wherein the current height is determined based on the initial height of the scanning bed and a vertical relative displacement of the scanning bed from an initial position to a current position.

12. The method of claim 8, wherein the horizontal position of the body surface measuring point under the initial height is determined based on a horizontal position of a baseline provided on the scanning bed and a horizontal relative displacement of the scanning bed from an initial position to a current position, wherein the baseline is provided such that baseline is parallel with a short side of the scanning bed.

13. The method of claim 8, wherein determining the measuring projection angle comprises:
acquiring a positioning projection angle when an image of a baseline as captured in the first image capturing device matches the positioning line predetermined in the first image capturing device, the baseline being disposed on the scanning bed and being parallel with a short side of the scanning bed, wherein the positioning projection angle is an angle of the line connecting the baseline and the first image capturing device with respect to its projection on the scanning bed; and
using the positioning projection angle as the measuring projection angle.

* * * * *